US00PP36531P2

(12) United States Plant Patent
Stöver

(10) Patent No.: US PP36,531 P2
(45) Date of Patent: Mar. 4, 2025

(54) ***PETUNIA-CALIBRACHOA HYBRID* PLANT NAMED 'KLECA23830'**

(50) Latin Name: ***Petunia* x *Calibrachoa* hybrid**
Varietal Denomination: KLECA23830

(71) Applicant: Klemm+Sohn GmbH & Co. KG, Stuttgart (DE)

(72) Inventor: Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 18/768,272

(22) Filed: Jul. 10, 2024

(51) Int. Cl.
*A01H 5/02* (2018.01)
*A01H 6/82* (2018.01)

(52) U.S. Cl.
USPC ..... Plt./356.11

(58) Field of Classification Search
USPC ..... Plt./413, 263.1, 356.1, 356.11
See application file for complete search history.

(56) References Cited

U.S. PATENT DOCUMENTS

PP25,287 P2 2/2015 Klemm et al.
PP25,418 P3 * 4/2015 Ui ..... A01H 6/82 Plt./356.11
PP26,332 P3 1/2016 Ui et al.

* cited by examiner

*Primary Examiner* — Karen M Redden
(74) *Attorney, Agent, or Firm* — COOLEY LLP

(57) ABSTRACT

A new Petchoa plant particularly distinguished by having large white flowers and an upright habit, is disclosed.

1 Drawing Sheet

Genus and species: *Petunia* x *Calibrachoa* hybrid.
Variety denomination: 'KLECA23830'.

BACKGROUND OF THE NEW PLANT

The present invention comprises a new and distinct variety of *Petunia* x *Calibrachoa* hybrid, commonly known as Petchoa, and hereinafter referred to by the variety name 'KLECA23830'. 'KLECA23830' originated from a controlled-cross between the female variety SuperCal® Blushing Pink (also known as 'SAKPXC008', U.S. Plant Pat. No. 25,418) and the male *Calibrachoa* variety 'KLECA12235' (U.S. Plant Pat. No. 25,287).

In August 2017, the female variety SuperCal® Blushing Pink and the male variety 'KLECA12235' were crossed via a controlled-cross in Stuttgart, Germany and seeds were obtained. The seeds were sown and plants were grown for evaluation. A plant line was selected in May 2018 and subsequently named 'KLECA23830'. 'KLECA23830' was first vegetatively propagated by cuttings in Stuttgart, Germany. 'KLECA23830' was found to reproduce true to type in successive generations of asexual propagation via cuttings.

SUMMARY

The following are the most outstanding and distinguishing characteristics of this new variety when grown under normal horticultural practices in Stuttgart, Germany.

1. Large, white flowers; and
2. Upright plant habit.

DESCRIPTION OF THE PHOTOGRAPH

This new Petchoa plant is illustrated by the accompanying photograph which shows a close-up of the whole plant. The photograph is of a 14-week-old-plant grown indoors in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLECA23830'. The data which define these characteristics were collected from asexual reproductions carried out in Stuttgart, Germany. Data was collected on 8-week old plants after transplant in Stuttgart, Germany. Color references are to The R.H.S. Colour Chart of The Royal Horticultural Society of London (R.H.S.), 5$^{th}$ edition (2007).

Classification:
- *Family*.—Solanaceae.
- *Species*.—*Petunia* x *Calibrachoa* hybrid.
- *Common name*.—Petchoa.

Parentage:
- *Female*.—SuperCal® Blushing Pink (also known as 'SAKPXC008', U.S. Plant Pat. No. 25,418).
- *Male*.—'KLECA12235' (U.S. Plant Pat. No. 25,287).

Plant description:
- *Life cycle*.—Annual.
- *Form*.—Short lived subshrub.
- *Habit*.—Upright.
- *Height* (*from soil line to top of foliage*).—17.0 cm.
- *Spread*.—40.0 cm.

Propagation:
- *Type cuttings*.—Tip cuttings.
- *Time to produce a rooted cutting*.—3 weeks.

Stems:
- *Stem color*.—RHS 144B.
- *Pubescence*.—Present.

*Pubescence color*.—RHS 145C.
*Stem diameter*.—0.3 cm.
*Stem length*.—From soil line to first node: 0.7 cm. Total length: 23.0 cm.
*Internode length*.—2.0 cm.

Leaves:
*Arrangement*.—Alternate.
*Shape*.—Elliptic.
*Apex*.—Broad acute.
*Base*.—Attenuate.
*Margin*.—Entire.
*Surface texture*.—Smooth.
*Surface pubescence*.—Absent.
*Venation*.—Pinnate.
*Venation color*.—Upper surface: RHS 146C. Lower surface: RHS 146D.
*Length*.—4.0 cm.
*Width*.—1.2 cm.
*Color*.—Upper surface: RHS 137A. Lower surface: RHS 137C.
*Fragrance*.—Absent.

Flowers:
*Flowering habit*.—Continuous.
*Flower type*.—Single.
*Flowering requirements*.—Natural sunlight.
*Duration of flowers*.—6 days.
*Corolla texture (both surfaces)*.—Smooth.
*Corolla*.—Rotate.
*Shape*.—Funnel form.
*Fragrance*.—Absent.
*Number of flowers per plant*.—15.

Flower buds (before opening):
*Surface*.—Smooth.
*Length*.—2.5 cm.
*Diameter*.—0.6 cm.
*Shape*.—Irregular to oblong.
*Color*.—RHS 150B.
*Typical number per plant*.—12.

Peduncle:
*Length*.—2.8 cm.
*Diameter*.—0.2 cm.
*Color*.—RHS 145A.
*Texture*.—Smooth.
*Anthocyanin color*.—Absent.

Flower description:
*Flower depth*.—2.9 cm.
*Flower tube length*.—2.6 cm.
*Flower tube diameter*.—0.8 cm.
*Flower diameter*.—5.2 cm.
*Flower throat diameter*.—1.2 cm.
*Pedicel color*.—RHS 145A.
*Calyx*.—RHS 146C.

Sepals:
*Quantity*.—5.
*Shape*.—Lanceolate.
*Texture*.—Smooth.
*Apex*.—Acute.
*Margin*.—Entire.
*Length*.—1.6 cm.
*Diameter*.—0.3 cm.
*Sepal color*.—Upper surface: RHS N137A. Lower surface: RHS 137C.

Petals:
*Shape*.—Reniform.
*Quantity*.—5, fused.
*Length*.—2.3 cm.
*Apex*.—Obtuse.
*Margin*.—Entire.
*Base*.—Wide open, fused.
*Pubescence*.—Absent.
*Lobe length*.—2.2 cm.
*Lobe width*.—2.8 cm.
*Color*.—Lobe color: Upper surface: RHS NN155C and RHS 70A of throat. Lower surface: RHS NN155C. Corolla tube color: Inner: RHS 9A and RHS 70A of veins. Outer: RHS 150C.
*Fragrance*.—Absent.
*Lobing intensity*.—Moderate.
*Vein intensity*.—Moderate to high.

Reproductive organs:
*Stamen*.—Quantity: 5. Anther color: RHS 10A. Anther length: 0.2 cm. Filament length: 1 cm. Filament color: RHS 10D. Pollen amount: Sparse. Pollen color: RHS 10B.
*Pistil*.—Quantity: 1. Length: 1.5 cm. Ovary: Superior. Placenta arrangement: Free, central. Stigma color: RHS 144A. Stigma shape: Rounded. Style length: 1.3 cm. Style color: RHS 145B.

Fruit/seed set: None.
Disease/insect resistance: None observed.

COMPARISON WITH PARENTAL LINES AND KNOWN VARIETY

'KLECA23830' is distinguished from its parents as described in Table 1:

TABLE 1

Comparison with Parental Lines

| Trait | Variety 'KLECA23830' | Female parent SuperCal ® Blushing Pink | Male parent 'KLECA12235' |
|---|---|---|---|
| Flower color | RHS NN155C + 70A | RHS 65C | RHS NN155D |
| Growth habit | Upright | Very upright | Very flat |

'KLECA23830' is most similar to SuperCal® Cherry Improved (also known as 'SAKPXC012', U.S. Plant Pat. No. 26,332). Differences between the two varieties are described in Table 2:

TABLE 2

Comparison with Similar Variety

| Trait | Variety 'KLECA23830' | SuperCal ® Cherry Improved |
|---|---|---|
| Flower color | RHS NN155C + 70A | Red-purple RHS N57 |

What is claimed is:

1. A new and distinct *Petunia-Calibrachoa* hybrid plant named 'KLECA23830' as shown and described herein.

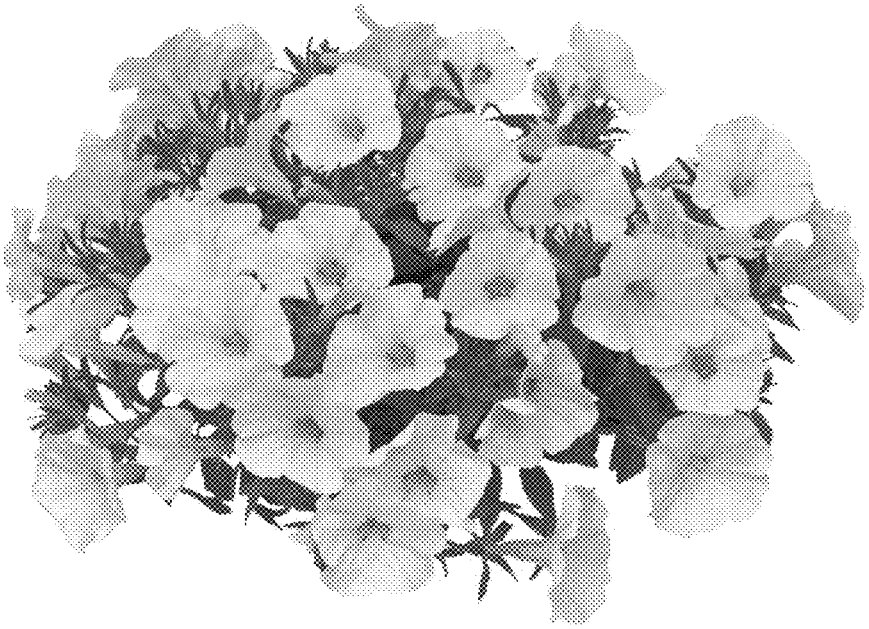

* * * * *